(12) United States Patent
Guo et al.

(10) Patent No.: US 8,192,974 B1
(45) Date of Patent: Jun. 5, 2012

(54) GLUCANASE HAVING INCREASED ENZYME ACTIVITY AND THERMOSTABILITY

(75) Inventors: Rey-Ting Guo, Taipei (TW); Jian-Wen Huang, Taipei (TW); Ya-Shan Cheng, Taipei (TW); Tzu-Hui Wu, Taipei (TW); Hui-Lin Lai, Taipei (TW); Cheng-Yen Lin, Taipei (TW)

(73) Assignee: Genozyme Biotech, Inc., Taipei (TW)

( * ) Notice: Subject to any disclaimer, the term of this patent is extended or adjusted under 35 U.S.C. 154(b) by 0 days.

(21) Appl. No.: 13/153,618

(22) Filed: Jun. 6, 2011

(30) Foreign Application Priority Data

Mar. 9, 2011  (TW) .................................. 100107992

(51) Int. Cl.
*C12N 9/42* (2006.01)

(52) U.S. Cl. ........................................................ 435/209

(58) Field of Classification Search .................... 435/209
See application file for complete search history.

(56) References Cited

U.S. PATENT DOCUMENTS 7,527,958 B2 * 5/2009 Shyur et al. .................... 435/201

OTHER PUBLICATIONS

Cheng et al. Biochemistry (Jul. 9, 2002) vol. 41, No. 27, pp. 8759-8766.*

* cited by examiner

*Primary Examiner* — Tekchand Saidha
(74) *Attorney, Agent, or Firm* — Kirton McConkie; Evan R. Witt (57) ABSTRACT

A glucanase having increased enzyme activity and thermostability is disclosed. The glucanase comprises a modified amino acid sequence of SEQ ID NO: 2, wherein valine at position 18 is substituted with tyrosine and tryptophan at position 203 is substituted with tyrosine.

8 Claims, 5 Drawing Sheets

```
atggttagcgcaaaggattttagcggtgccgaactctacacgttagaagaagttcagtacggtaagtttgaagcccgtatgaagatggca
 M  V  S  A  K  D  F  S  G  A  E  L  Y  T  L  E  E  V  Q  Y  G  K  F  E  A  R  M  K  M  A gccgcatcgggaacagtcagttccatgttcctctaccagaatggttccgaaatcgccgatggaaggccctgggtagaagtggatattgaa
 A  A  S  G  T  V  S  S  M  F  L  Y  Q  N  G  S  E  I  A  D  G  R  P  W  V  E  V  D  I  E gttctcggcaagagtccgggcagtttccagtccaacatcattaccggtaaggccggcgcacaaaagactagcgaaaagcaccatgctgtt
 V  L  G  K  S  P  G  S  F  Q  S  N  I  I  T  G  K  A  G  A  Q  K  T  S  E  K  H  H  A  V agccccgccgccgatcaggctttccacacctacggtctcgaatggactccgaattacgtccgctggactgttgacggtcaggaagtccgc
 S  P  A  A  D  Q  A  F  H  T  Y  G  L  E  W  T  P  N  Y  V  R  W  T  V  D  G  Q  E  V  R aagacggaaggtggccaggtttccaacttgacaggtacacagggactccgttttaacctttggtcgtctgagagtgcggcttgggttggc
 K  T  E  G  G  Q  V  S  N  L  T  G  T  Q  G  L  R  F  N  L  W  S  S  E  S  A  A  W  V  G cagttcgatgaatcaaagcttccgcttttccagttcatcaactgggtcaaggtttataagtatacgccgggccagggcgaaggcggcagc
 Q  F  D  E  S  K  L  P  L  F  Q  F  I  N  W  V  K  V  Y  K  Y  T  P  G  Q  G  E  G  G  S gactttacgcttgactggaccgacaattttgacacgtttgatggctccgctggggcaagggtgactggacatttgacggtaaccgtgtc
 D  F  T  L  D  W  T  D  N  F  D  T  F  D  G  S  R  W  G  K  G  D  W  T  F  D  G  N  R  V gacctcaccgacaagaacatctactccagagatggcatgttgatcttggccttgaccagaaaaggtcaagagagcttcaacggccaagtt
 D  L  T  D  K  N  I  Y  S  R  D  G  M  L  I  L  A  L  T  R  K  G  Q  E  S  F  N  G  Q  V ccaagagatgacgaacctgctccataa  -SEQ ID NO: 1
 P  R  D  D  E  P  A  P  *   -SEQ ID NO: 2
```

FIG. 1

| Mutant | Primer sequence (5' --> 3') |
|--------|------------------------------|
| V18Y | 5'- CCGCTGGGGCAAGGGTGACTACACATTTGACGGTAACCGTGTCG -3' |
| W203Y | 5'- AACTCTACACGTTAGAAGAATACCAGTACGGTAAGTTTGAAGC -3' |

FIG. 2

```
atggttagcgcaaaggatttttagcggtgccgaactctacacgttagaagaagttcagtacggtaagtttgaagcccgtatgaagatggca
 M  V  S  A  K  D  F  S  G  A  E  L  Y  T  L  E  E [Y] Q  Y  G  K  F  E  A  R  M  K  M  A gccgcatcgggaacagtcagttccatgttcctctaccagaatggttccgaaatcgccgatggaaggccctgggtagaagtggatattgaa
 A  A  S  G  T  V  S  S  M  F  L  Y  Q  N  G  S  E  I  A  D  G  R  P  W  V  E  V  D  I  E gttctcggcaagagtccgggcagtttccagtccaacatcattaccggtaaggccggcgcacaaaagactagcgaaaagcaccatgctgtt
 V  L  G  K  S  P  G  S  F  Q  S  N  I  I  T  G  K  A  G  A  Q  K  T  S  E  K  H  H  A  V agccccgccgccgatcaggcttccacacctacggtctcgaatggactccgaattacgtccgctggactgttgacggtcaggaagtccgc
 S  P  A  A  D  Q  A  F  H  T  Y  G  L  E  W  T  P  N  Y  V  R  W  T  V  D  G  Q  E  V  R aagacggaaggtggccaggtttccaacttgacaggtacacagggactccgttttaacctttggtcgtctgagagtgcggcttgggttggc
 K  T  E  G  G  Q  V  S  N  L  T  G  T  Q  G  L  R  F  N  L  W  S  S  E  S  A  A  N  V  G cagttcgatgaatcaaagcttccgcttttccagttcatcaactgggtcaaggtttataagtatacgccgggccagggcgaaggcggcagc
 Q  F  D  E  S  K  L  P  L  F  Q  F  I  N  W  V  K  V  Y  K  Y  T  P  G  Q  G  E  G  G  S gactttacgcttgactggaccgacaattttgacacgtttgatggctcccgctggggcaaggggtgactggacatttgacggtaaccgtgtc
 D  F  T  L  D  W  T  D  N  F  D  T  F  D  G  S  R  W  G  K  G  D  W  T  F  D  G  N  R  V gacctcaccgacaagaacatctactccagagatggcatgttgatcttggccttgaccagaaaaggtcaagagagcttcaacggccaagtt
 D  L  T  D  K  N  I  Y  S  R  D  G  M  L  I  L  A  L  T  R  K  G  Q  E  S  F  N  G  Q  V ccaagagatgacgaacctgctccataa                -SEQ ID NO: 3
 P  R  D  D  E  P  A  P  *                   -SEQ ID NO: 4
```

FIG. 3

```
atggttagcgcaaaggatttttagcggtgccgaactctacacgttagaagaagttcagtacggtaagtttgaagcccgtatgaagatggca
 M  V  S  A  K  D  F  S  G  A  E  L  Y  T  L  E  E  V  Q  Y  G  K  F  E  A  R  M  K  M  A gccgcatcgggaacagtcagttccatgttcctctaccagaatggttccgaaatcgccgatggaaggccctgggtagaagtggatattgaa
 A  A  S  G  T  V  S  S  M  F  L  Y  Q  N  G  S  E  I  A  D  G  R  P  W  V  E  V  D  I  E gttctcggcaagagtccgggcagtttccagtccaacatcattaccggtaaggccggcgcacaaaagactagcgaaaagcaccatgctgtt
 V  L  G  K  S  P  G  S  F  Q  S  N  I  I  T  G  K  A  G  A  Q  K  T  S  E  K  H  H  A  V agccccgccgccgatcaggcttccacacctacggtctcgaatggactccgaattacgtccgctggactgttgacggtcaggaagtccgc
 S  P  A  A  D  Q  A  F  H  T  Y  G  L  E  W  T  P  N  Y  V  R  W  T  V  D  G  Q  E  V  R aagacggaaggtggccaggtttccaacttgacaggtacacagggactccgttttaacctttggtcgtctgagagtgcggcttgggttggc
 K  T  E  G  G  Q  V  S  N  L  T  G  T  Q  G  L  R  F  N  L  W  S  S  E  S  A  A  N  V  G cagttcgatgaatcaaagcttccgcttttccagttcatcaactgggtcaaggtttataagtatacgccgggccagggcgaaggcggcagc
 Q  F  D  E  S  K  L  P  L  F  Q  F  I  N  W  V  K  V  Y  K  Y  T  P  G  Q  G  E  G  G  S gactttacgcttgactggaccgacaattttgacacgtttgatggctcccgctggggcaaggggtgac[Y]catttgacggtaaccgtgtc
 D  F  T  L  D  W  T  D  N  F  D  T  F  D  G  S  R  W  G  K  G  D [Y] T  F  D  G  N  R  V gacctcaccgacaagaacatctactccagagatggcatgttgatcttggccttgaccagaaaaggtcaagagagcttcaacggccaagtt
 D  L  T  D  K  N  I  Y  S  R  D  G  M  L  I  L  A  L  T  R  K  G  Q  E  S  F  N  G  Q  V ccaagagatgacgaacctgctccataa                -SEQ ID NO: 5
 P  R  D  D  E  P  A  P  *                   -SEQ ID NO: 6
```

| Protein expressed in *E. coli* | Specific activity (U/mg) |
|---|---|
| WT | 5694 |
| V18Y | 6520 |
| W203Y | 9263 |
| V18Y/W203Y | 9967 |

SEQUENCE LISTING

<160> NUMBER OF SEQ ID NOS: 8

<210> SEQ ID NO 1
<211> LENGTH: 747
<212> TYPE: DNA
<213> ORGANISM: Fibrobacter succinogenes

<400> SEQUENCE: 1

```
atggttagcg caaaggattt tagcggtgcc gaactctaca cgttagaaga agttcagtac      60
ggtaagtttg aagcccgtat gaagatggca gccgcatcgg gaacagtcag ttccatgttc     120
ctctaccaga atggttccga aatcgccgat ggaaggccct gggtagaagt ggatattgaa     180
gttctcggca agagtccggg cagtttccag tccaacatca ttaccggtaa ggccggcgca     240
caaaagacta gcgaaaagca ccatgctgtt agccccgccg ccgatcaggc tttccacacc     300
```

```
tacggtctcg aatggactcc gaattacgtc cgctggactg ttgacggtca ggaagtccgc    360
aagacggaag gtggccaggt ttccaacttg acaggtacac agggactccg ttttaacctt    420
tggtcgtctg agagtgcggc ttgggttggc cagttcgatg aatcaaagct tccgcttttc    480
cagttcatca actgggtcaa ggtttataag tatacgccgg gccagggcga aggcggcagc    540
gactttacgc ttgactggac cgacaatttt gacacgtttg atggctcccg ctggggcaag    600
ggtgactgga catttgacgg taaccgtgtc gacctcaccg acaagaacat ctactccaga    660
gatggcatgt tgatcttggc cttgaccaga aaaggtcaag agagcttcaa cggccaagtt    720
ccaagagatg acgaacctgc tccataa                                        747
```

<210> SEQ ID NO 2
<211> LENGTH: 248
<212> TYPE: PRT
<213> ORGANISM: Fibrobacter succinogenes

<400> SEQUENCE: 2

```
Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Ser Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125

Asn Leu Thr Gly Thr Gln Gly Leu Arg Phe Asn Leu Trp Ser Ser Glu
    130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Trp Thr Phe Asp Gly Asn
        195                 200                 205

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro
                245
```

<210> SEQ ID NO 3
<211> LENGTH: 747
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 3

```
atggttagcg caaaggattt tagcggtgcc gaactctaca cgttagaaga ataccagtac    60
ggtaagtttg aagcccgtat gaagatggca gccgcatcgg gaacagtcag ttccatgttc   120
ctctaccaga atggttccga atcgccgat ggaaggccct gggtagaagt ggatattgaa    180
gttctcggca agagtccggg cagtttccag tccaacatca ttaccggtaa ggccggcgca   240
caaaagacta gcgaaaagca ccatgctgtt agccccgccg ccgatcaggc tttccacacc   300
tacggtctcg aatggactcc gaattacgtc cgctggactg ttgacggtca ggaagtccgc   360
aagacggaag gtggccaggt ttccaacttg acaggtacac agggactccg tttaaccctt   420
tggtcgtctg agagtgcggc ttgggttggc cagttcgatg aatcaaagct tccgcttttc   480
cagttcatca actgggtcaa ggtttataag tatacgccgg gccagggcga aggcggcagc   540
gactttacgc ttgactggac cgacaatttt gacacgtttg atggctcccg ctggggcaag   600
ggtgactgga catttgacgg taaccgtgtc gacctcaccg acaagaacat ctactccaga   660
gatggcatgt tgatcttggc cttgaccaga aaaggtcaag agagcttcaa cggccaagtt   720
ccaagagatg acgaacctgc tccataa                                       747
```

<210> SEQ ID NO 4
<211> LENGTH: 248
<212> TYPE: PRT
<213> ORGANISM: Artificial Sequence
<220> FEATURE:
<223> OTHER INFORMATION: Sequence synthetically translated from SEQ. ID. NO: 3

<400> SEQUENCE: 4

```
Met Val Ser Ala Lys Asp Phe Ser Gly Ala Glu Leu Tyr Thr Leu Glu
1               5                  10                  15

Glu Tyr Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
        35                  40                  45

Ala Asp Gly Arg Pro Trp Val Glu Val Asp Ile Glu Val Leu Gly Lys
    50                  55                  60

Ser Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125

Asn Leu Thr Gly Thr Gln Gly Leu Arg Phe Asn Leu Trp Ser Ser Glu
    130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Trp Thr Phe Asp Gly Asn
        195                 200                 205

Arg Val Asp Leu Thr Asp Lys Asn Ile Tyr Ser Arg Asp Gly Met Leu
```

```
                   210                 215                 220
Ile Leu Ala Leu Thr Arg Lys Gly Gln Glu Ser Phe Asn Gly Gln Val
225                 230                 235                 240

Pro Arg Asp Asp Glu Pro Ala Pro
                245
```

<210> SEQ ID NO 5
<211> LENGTH: 747
<212> TYPE: DNA
<213> ORGANISM: Artificial Sequence
<220> FEATURE:
<223> OTHER INFORMATION: Synthetically generated DNA encoding a modified enzyme

<400> SEQUENCE: 5

```
atggttagcg caaaggattt tagcggtgcc gaactctaca cgttagaaga agttcagtac    60
ggtaagtttg aagcccgtat gaagatggca gccgcatcgg gaacagtcag ttccatgttc   120
ctctaccaga atggttccga aatcgccgat ggaaggccct gggtagaagt ggatattgaa   180
gttctcggca agagtccggg cagtttccag tccaacatca ttaccggtaa ggccggcgca   240
caaaagacta gcgaaaagca ccatgctgtt agccccgccg ccgatcaggc tttccacacc   300
tacggtctcg aatggactcc gaattacgtc cgctggactg ttgacggtca ggaagtccgc   360
aagacggaag gtgccaggt ttccaacttg acaggtacac agggactccg ttttaacctt    420
tggtcgtctg agagtgcggc ttgggttggc cagttcgatg aatcaaagct tccgcttttc   480
cagttcatca actgggtcaa ggtttataag tatacgccgg ccagggcga aggcggcagc    540
gactttacgc ttgactggac cgacaatttt gacacgtttg atggctcccg ctggggcaag   600
ggtgactaca catttgacgg taaccgtgtc gacctcaccg acaagaacat ctactccaga   660
gatggcatgt tgatcttggc cttgaccaga aaaggtcaag agagcttcaa cggccaagtt   720
ccaagagatg acgaacctgc tccataa                                       747
```

<210> SEQ ID NO 6
<211> LENGTH: 248
<212> TYPE: PRT
<213> ORGANISM: Artificial Sequence
<220> FEATURE:
<223> OTHER INFORMATION: Sequence synthetically translated from SEQ. ID. NO: 5

<400> SEQUENCE: 6

```
Met Val Ser Ala Lys Asp Phe Ser Gly Ala Glu Leu Tyr Thr Leu Glu
1               5                   10                  15

Glu Val Gln Tyr Gly Lys Phe Glu Ala Arg Met Lys Met Ala Ala Ala
                20                  25                  30

Ser Gly Thr Val Ser Ser Met Phe Leu Tyr Gln Asn Gly Ser Glu Ile
            35                  40                  45

Ala Asp Gly Arg Pro Trp Val Glu Val Asp Ile Glu Val Leu Gly Lys
        50                  55                  60

Ser Pro Gly Ser Phe Gln Ser Asn Ile Ile Thr Gly Lys Ala Gly Ala
65                  70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125
```

```
Asn Leu Thr Gly Thr Gln Gly Leu Arg Phe Asn Leu Trp Ser Ser Glu
            130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Tyr Thr Phe Asp Gly Asn
            195                 200                 205

Arg Val Asp Leu Thr Asp Lys Asn Ile Tyr Ser Arg Asp Gly Met Leu
            210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro
            245
```

<210> SEQ ID NO 7
<211> LENGTH: 747
<212> TYPE: DNA
<213> ORGANISM: Artificial Sequence
<220> FEATURE:
<223> OTHER INFORMATION: Synthetically generated DNA encoding a modified enzyme

<400> SEQUENCE: 7

```
atggttagcg caaaggattt tagcggtgcc gaactctaca cgttagaaga ataccagtac    60
ggtaagtttg aagcccgtat gaagatggca gccgcatcgg gaacagtcag ttccatgttc   120
ctctaccaga atggttccga aatcgccgat ggaaggccct gggtagaagt ggatattgaa   180
gttctcggca agagtccggg cagtttccag tccaacatca ttaccggtaa ggccggcgca   240
caaaagacta gcgaaaagca ccatgctgtt agccccgccg ccgatcaggc tttccacacc   300
tacggtctcg aatggactcc gaattacgtc cgctggactg ttgacggtca ggaagtccgc   360
aagacggaag gtggccaggt ttccaacttg acaggtacac agggactccg ttttaacctt   420
tggtcgtctg agagtgcggc ttgggttggc cagttcgatg aatcaaagct tccgcttttc   480
cagttcatca actgggtcaa ggtttataag tatcgccgg ccagggcga aggcggcagc    540
gactttacgc ttgactggac cgacaatttt gacacgtttg atggctcccg ctggggcaag   600
ggtgactaca catttgacgg taaccgtgtc gacctcaccg acaagaacat ctactccaga   660
gatggcatgt tgatcttggc cttgaccaga aaaggtcaag agagcttcaa cggccaagtt   720
ccaagagatg acgaacctgc tccataa                                       747
```

<210> SEQ ID NO 8
<211> LENGTH: 248
<212> TYPE: PRT
<213> ORGANISM: Artificial Sequence
<220> FEATURE:
<223> OTHER INFORMATION: Sequence synthetically translated from SEQ. ID. NO: 7

<400> SEQUENCE: 8

```
Met Val Ser Ala Lys Asp Phe Ser Gly Ala Glu Leu Tyr Thr Leu Glu
1               5                   10                  15

Glu Tyr Gln Tyr Gly Lys Phe Glu Ala Arg Met Lys Met Ala Ala Ala
            20                  25                  30

Ser Gly Thr Val Ser Ser Met Phe Leu Tyr Gln Asn Gly Ser Glu Ile
            35                  40                  45
```

-continued

```
Ala Asp Gly Arg Pro Trp Val Glu Val Asp Ile Glu Val Leu Gly Lys
    50                  55                  60

Ser Pro Gly Ser Phe Gln Ser Asn Ile Ile Thr Gly Lys Ala Gly Ala
65              70                  75                      80

Gln Lys Thr Ser Glu Lys His His Ala Val Ser Pro Ala Ala Asp Gln
                85              90                      95

Ala Phe His Thr Tyr Gly Leu Glu Trp Thr Pro Asn Tyr Val Arg Trp
            100             105                 110

Thr Val Asp Gly Gln Glu Val Arg Lys Thr Glu Gly Gly Gln Val Ser
        115             120                 125

Asn Leu Thr Gly Thr Gln Gly Leu Arg Phe Asn Leu Trp Ser Ser Glu
    130             135             140

Ser Ala Ala Trp Val Gly Gln Phe Asp Glu Ser Lys Leu Pro Leu Phe
145             150             155                         160

Gln Phe Ile Asn Trp Val Lys Val Tyr Lys Tyr Thr Pro Gly Gln Gly
            165             170                     175

Glu Gly Gly Ser Asp Phe Thr Leu Asp Trp Thr Asp Asn Phe Asp Thr
            180             185                 190

Phe Asp Gly Ser Arg Trp Gly Lys Gly Asp Tyr Thr Phe Asp Gly Asn
        195             200                 205

Arg Val Asp Leu Thr Asp Lys Asn Ile Tyr Ser Arg Asp Gly Met Leu
    210             215                 220

Ile Leu Ala Leu Thr Arg Lys Gly Gln Glu Ser Phe Asn Gly Gln Val
225             230             235                         240

Pro Arg Asp Asp Glu Pro Ala Pro
            245
```

GLUCANASE HAVING INCREASED ENZYME ACTIVITY AND THERMOSTABILITY

FIELD OF THE INVENTION

The present invention relates to a glucanase, and more particularly to a 1,3-1,4-β-D-glucanase.

BACKGROUND OF THE INVENTION 1,3-1,4-β-D-glucanase (lichenase, EC 3.2.1.73) can specifically hydrolyze 1,4-β-D-glucosidic bonds adjacent to 1,3-β-linkages in lichenan or β-D-glucans. The major products of the hydrolysis reaction including cellotriose, cellotetraose and cellopentaose are important nutrients for animals. The enzyme draws much attention because of its broad spectrum of industrial applications. Supplementation of 1,3-1,4-β-D-glucanase in nonruminal animal feed largely increases the feed conversion efficiency and growth rate. In addition to animal feed, 1,3-1,4-β-D-glucanase is also used in beer industry as the enzyme can degrade the high molecular mass β-glucans to prevent reduced yields of extracts, inefficient wort separation and beer filtration. The pelleting and expansion processes in feed industry are performed at 65 to 90° C., and the optimal temperature for the malting processes in beer manufacture is between 50 and 70° C. Therefore, to increase thermostability of 1,3-1,4-β-D-glucanase is highly demanded for various industrial applications.

There are two approaches to obtain a highly thermostable enzyme. The first is to directly clone the enzyme-coding genes from hyperthermophiles and to express the proteins in industrial strains. For instance, *Thermotoga maritima* cellulase 12A (TmCell2A) that belongs to the GH12 family of glycoside hydrolases shows the strongest activity at 95° C. and has a pH optimum of 5. These characteristics make the enzyme highly valuable in various utilizations, since industrial processes such as plant waste treatments usually involve high temperature and low pH. Nevertheless, the hyperthermophile-derived enzymes usually exhibit low activities in physiological conditions which are between 20 and 37° C., and thus severely limit their applications in aquatic and nonruminal animals. These hyperthermophilic enzymes still need to be modified to meet the requirement for different industrial usages. The second approach to obtain a thermostable enzyme is to directly modify a less thermostable enzyme by genetic manipulations.

*Fibrobacter succinogenes* 1,3-1,4-β-D-glucanase is classified as a member of the family 16 glycosyl hydrolases and is the only naturally occurring circularly permuted β-glucanase, among bacterial glucanases with reverse protein domains. The C-terminal truncated *F. succinogenes* 1,3-1,4-β-D-glucanase (TF-glucanase; residues 1-248) exhibits a higher thermostability and enzymatic activity than the full-length enzyme. The structures of TF-glucanase apo-form and in complex with β-1,3-1,4-Cellotriose (CLTR) have been solved. TF-glucanase consists mainly of two 8-stranded antiparallel β-sheets that are arranged in a jellyroll β-sandwich structure. Residues E11, N44, E47, E56, E60, R137, N139, W141 and T204 are involved in a hydrogen bond network, and residues F40, Y42, W203 and F205 are involved in the stacking interaction between CLTR and TF-glucanase (−3, −2 and −1 subsites). This enzyme has also been well studied by mutagenesis and functional analyses. More importantly, the amounts of secreted TF-glucanase from *Pichia pastoris* fermentation was approaching 3 g/l by optimizing the codon usage, making the protein production meet the level of industrial manufacturing (range from 1 to 10 g/l). Accordingly, TF-glucanase is an excellent target for directed mutagenesis to be modified as a better product for industrial usage.

Therefore, the present invention directly mutated the TF-glucanase gene in attempt to improve the enzyme activity and thermostability.

SUMMARY OF THE INVENTION

An object of the present invention is to modify a glucanase by means of site-directed mutagenesis to efficiently increase the enzyme activity and thermostability, reduce the production costs and enhance the industrial value.

According to an aspect of the present invention, there is provided a glucanase comprising modified amino acid sequence of SEQ ID NO: 2, wherein valine at position 18 is substituted with tyrosine and tryptophan at position 203 is substituted with tyrosine.

In an embodiment, a gene encoding the amino acid sequence of SEQ ID NO: 2 is a C-terminal truncated Fsβ-glucanase gene isolated from *Fibrobacter succinogenes*. The glucanase is a 1,3-1,4-β-D-glucanase.

In an embodiment, the cellulase comprises an amino acid sequence of SEQ ID NO: 8.

According to another aspect of the present invention, there is provided a glucanase comprising modified amino acid sequence of SEQ ID NO: 2, wherein tryptophan at position 203 is substituted with tyrosine.

In an embodiment, a gene encoding the amino acid sequence of SEQ ID NO: 2 is a C-terminal truncated Fsβ-glucanase gene isolated from *Fibrobacter succinogenes*. The glucanase is a 1,3-1,4-β-D-glucanase.

In an embodiment, the cellulase comprises an amino acid sequence of SEQ ID NO: 6.

According to an additional aspect of the present invention, there is provided a glucanase comprising modified amino acid sequence of SEQ ID NO: 2, wherein valine at position 18 is substituted with tyrosine.

In an embodiment, a gene encoding the amino acid sequence of SEQ ID NO: 2 is a C-terminal truncated Fsβ-glucanase gene isolated from *Fibrobacter succinogenes*. The glucanase is a 1,3-1,4-β-D-glucanase.

In an embodiment, the cellulase comprises an amino acid sequence of SEQ ID NO: 4.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, a gene of Fsβ-glucanase, which encodes a protein of 1,3-1,4-β-D-glucanase, was isolated from *Fibrobacter succinogenes*. As known from the prior art of U.S. Pat. No. 7,037,696, the C-terminal truncated Fsβ-glucanase (TF-glucanase) exhibits a higher thermostability and enzyme activity than the full-length enzyme, and thus, this TF-glucanase gene was employed as the target gene for further modification based on the structural information of the enzyme. The enzyme modification process of the TF-glucanase is described in detail as follows.

Figure 1:
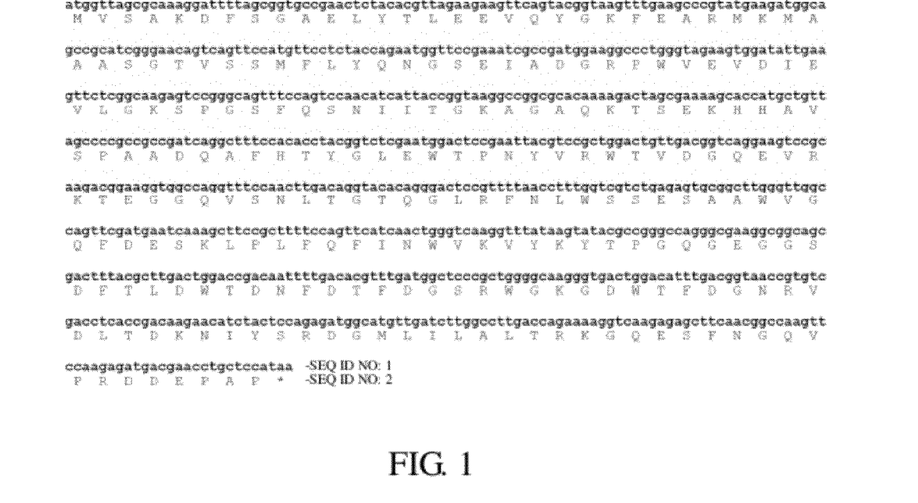
FIG. 1 shows the gene sequence and amino acid sequence of wild type TF-glucanase.

FIG. 1 shows the gene sequence and amino acid sequence of wild type TF-glucanase. The sequence length of TF-glucanase gene is 747 base pairs (SEQ ID NO: 1), which encodes a protein of 248 amino acids (SEQ ID NO: 2). The TF-glucanase gene shown in FIG. 1 was amplified by polymerase chain reaction (PCR) with forward primers 5'-GGTAT-TGAGGGTCGCGCGG CGGCGGCGGCGATGTTGGT-TAGCGCAAAGGATT-3' and reverse primer 5'-AGAG-GAGAGTTAGAGCCTTACGGAGCAGGTTCGTCATC-3', and then cloned into the pET32Xa/LIC vector.

Figure 2:
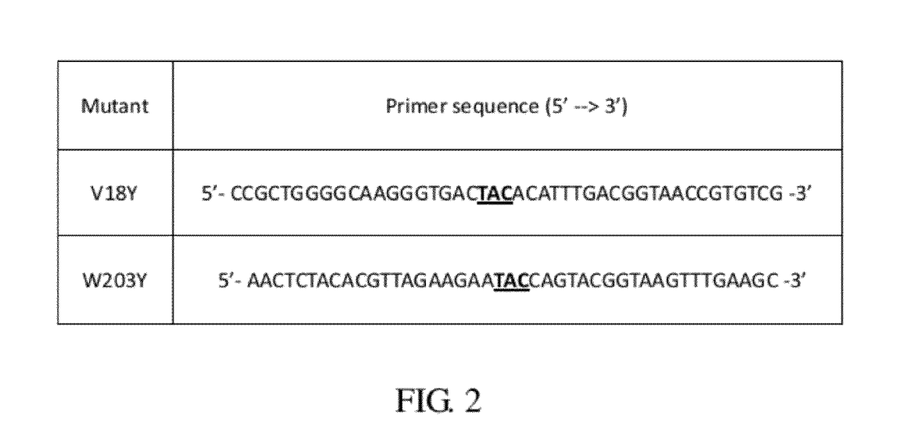
FIG. 2 shows the mutagenic primer sequences for the V18Y and W203Y mutants.
Figure 3:
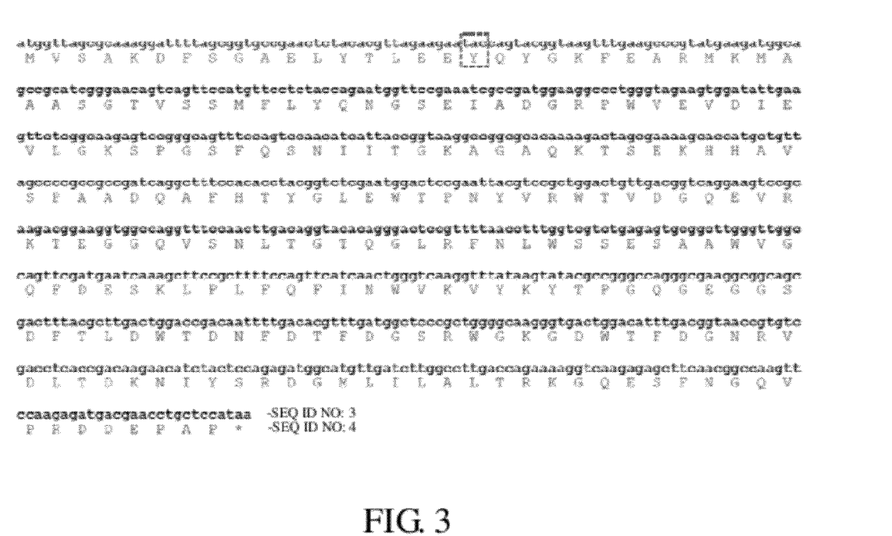
FIG. 3 shows the gene sequence and amino acid sequence of the V18Y mutant.
Figure 4:
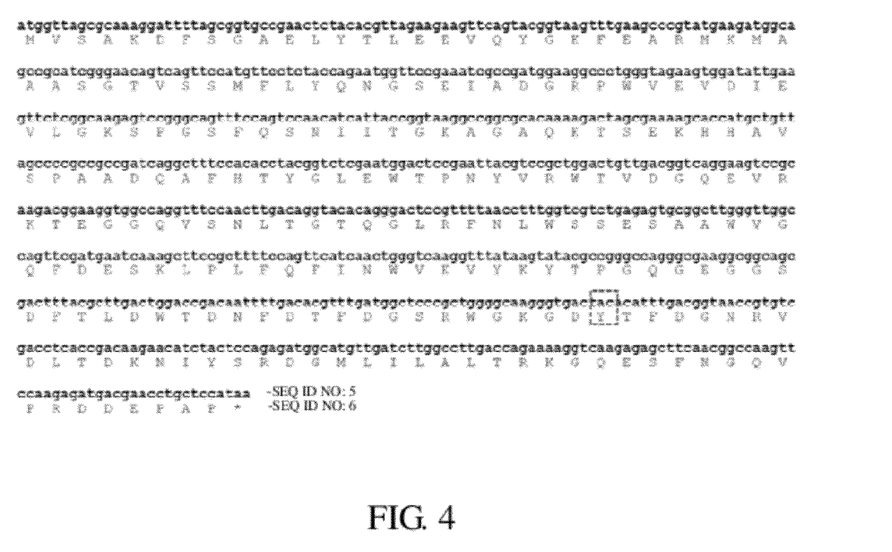
FIG. 4 shows the gene sequence and amino acid sequence of the W203Y mutant.
Figure 5:
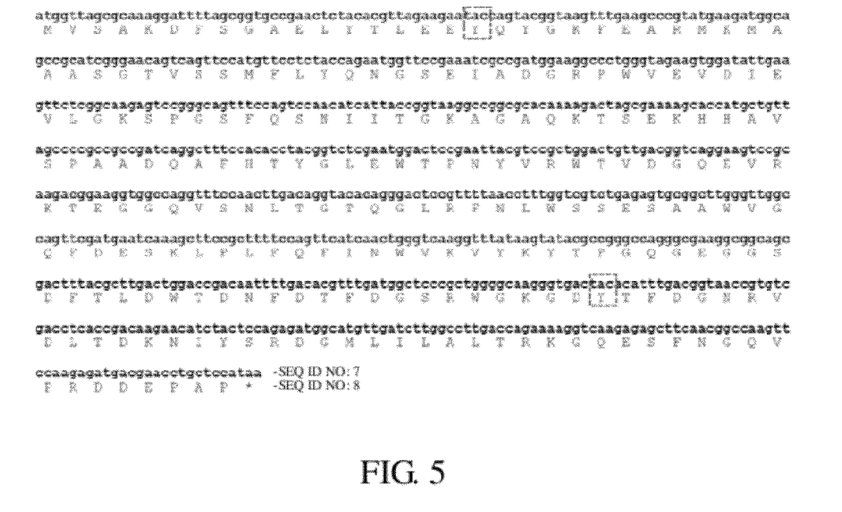
FIG. 5 shows the gene sequence and amino acid sequence of the V18Y/W203Y mutant.

In order to increase the specific activity and thermostability of TF-glucanase, the site-directed mutagenesis was performed to obtain the mutants including V18Y, W203Y and V18Y/W203Y, wherein V18Y means valine at position 18 was mutated into tyrosine, W203Y means tryptophan at position 203 was mutated into tyrosine, and V18Y/W203Y is a double mutant in which valine at position 18 was mutated into tyrosine and tryptophan at position 203 was mutated into tyrosine. These mutants were prepared by using Quick-Change site-directed mutagenesis kit (Agilent) with TF-glucanase-pET32Xa/LIC gene as the template, and the mutagenic primer sequences for these mutants were listed in FIG. 2. The mutant plasmids were transformed into *E. coli* and the mutant genes were confirmed by sequencing. FIGS. 3 to 5 show the gene sequence and amino acid sequence of V18Y, W203Y and V18Y/W203Y mutants, respectively, wherein the gene sequences were numbered as SEQ ID NO: 3, SEQ ID NO: 5, SEQ ID NO: 7, and the amino acid sequences were numbered as SEQ ID NO: 4, SEQ ID NO: 6, SEQ ID NO: 8, respectively.

The recombinant plasmids of wild type and mutant TF-glucanases were transformed into *E. coli* BL21 (DE3) competent cell, respectively, and the transformed strains were screened by LB plate with 100 μg/ml Ampicillin. The transformed strains were inoculated and cultured into 5 ml LB medium and then amplified into 200 ml LB medium. Finally, the culture was grown into 6 L LB medium and incubated at 37° C. until OD600 reached 0.6-0.8. The protein expression was induced by adding 1 mM IPTG for 3 hours. After that, the cells were collected by centrifugation at 6000 rpm for 10 min. The cells were lysed in lysis buffer by sonicator and then centrifuged at 16000 rpm for 30 min to collect supernatants for purification. For obtaining highly purified protein, the TF-glucanase protein was purified by FPLC system using $Ni^{2+}$ column and DEAE column. Finally, the TF-glucanase protein, which had above 95% purity, was concentrated up to 5 mg/ml in protein buffer (25 mM Tris and 150 mM NaCl, pH 7.5) and then was stored at −80° C.

The enzyme activity and thermostability of wild type and mutant TF-glucanases were further tested with the following process. 1 ml of enzyme solution (dissolved in 0.1 M sodium acetate, pH 5.0) was incubated with 1 ml substrate solution (1% β-glucan (w/v)) at 50° C. for 10 min. The reaction was stopped by adding 3 ml of DNS-reagent and the solution was boiled in water for 5 min to remove debris enzyme activity. After cooling in cold water bath for 5 min, the 540 nm absorbance of reaction solution was measured. The standard curve of enzyme activity was determined by 0-0.25 mg/ml glucose standard solution. One unit of β-glucanase activity was defined as the amount of enzyme required to liberate 1 μmol reducing sugar from β-glucan per minute per mg total soluble proteins under the assay conditions. As for the thermostability test, these TF-glucanases were pre-treated at several temperature points from 50° C. to 62° C., such as 50° C., 53° C., 55° C., 57° C., 59° C. and 62° C., for 2 min and then incubated in cold water bath for 5 min. The enzyme activities were obtained using the glucanase activity assay mentioned above.

Figure 6:
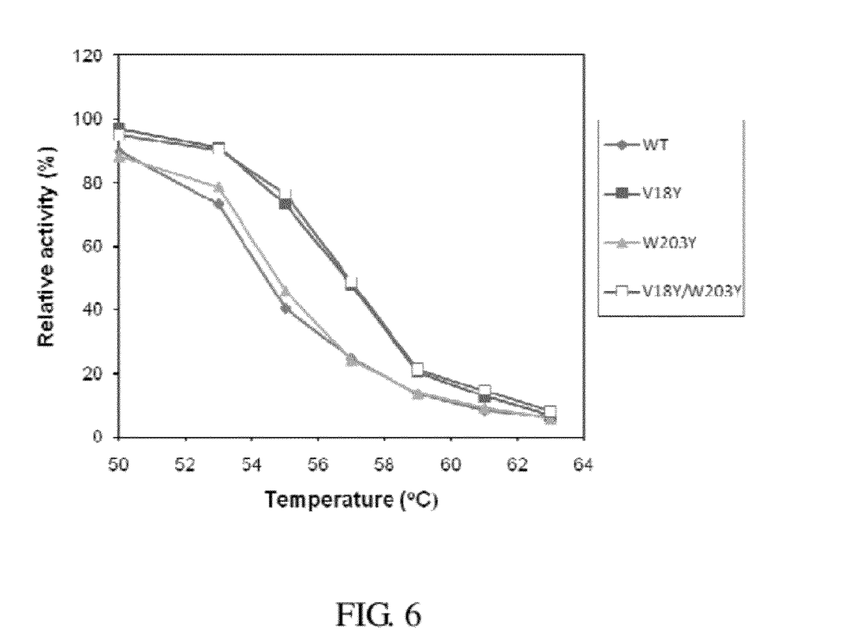
FIG. 6 shows the thermostability analysis of the wild type TF-glucanase protein and the V18Y, W203Y and V18Y/W203Y mutant proteins.

FIG. 6 shows the thermostability analysis of the wild type TF-glucanase protein and the V18Y, W203Y and V18Y/W203Y mutant proteins. It was observed that the V18Y and V18Y/W203Y mutants had better thermostability than the wild-type enzyme (WT). After the thermal treatment at 55° C., the wild-type enzyme and the W203Y mutant protein had only 40% relative activity but the V18Y and V18Y/W203Y mutant proteins still had 75% relative activity. Further, the W203Y mutant protein had the same Tm as the wild-type enzyme but the V18Y and V18Y/W203Y mutant proteins showed 2° C. increment of temperature tolerance (Tm, changed from 57 to 59° C.). As a result, the thermostability of TF-glucanase was improved when Val18 was mutated to tyrosine.

Figure 7:
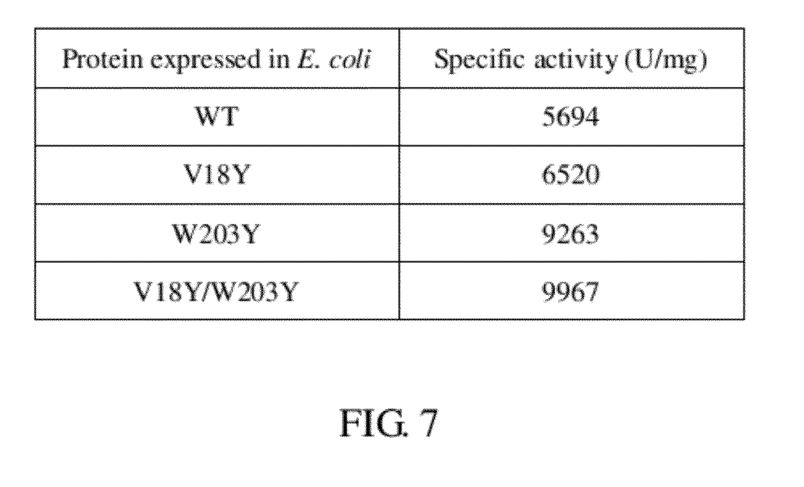
FIG. 7 shows the enzyme activity analysis of the wild type TF-glucanase protein and the V18Y, W203Y and V18Y/W203Y mutant proteins.

FIG. 7 shows the enzyme activity analysis of the wild type TF-glucanase protein and the V18Y, W203Y and V18Y/W203Y mutant proteins. The Barley β-glucan was used as the substrate in this study because there is no lichenan to be used as in the animal feed. The β-glucanase activity results were shown in FIG. 7 and the specific activities against Barley β-glucan of the wild-type, V18Y, W203Y, and V18Y/W203Y mutant proteins were 5694, 6520, 9263 and 9967 U/mg (100%, 114.5%, 162.7% and 175.0%). It was clear that the W203Y and V18Y/W203Y mutant proteins had at least 1.6-fold increase in enzyme activity when compared to the wild type enzyme. These results indicated that the enzyme activity of TF-glucanase was significantly improved when Trp203 was mutated to tyrosine.

From the above, the enzyme thermostability of TF-glucanase was improved when Val18 was mutated to tyrosine and the enzyme activity of TF-glucanase was improved when Trp203 was mutated to tyrosine. When both Val18 and Trp203 were mutated to tyrosine, the double mutant protein showed increased thermostability and enzyme activity as well, which also meant the two modification features resulted from V18Y and W203Y would not affect each other and were complementary to each other. Therefore, the V18Y/W203Y mutant is of much value to reduce the production cost and enhance the industrial application.

To test if the modified TF-glucanase protein can be expressed well in industrial expression system, *Pichia pas-* toris expression system was used. The wild type TF-glucanase gene and the V18Y, W203Y and V18Y/W203Y mutant genes were cloned into pPICZαA vector by EcoRI and NotI. Each plasmid DNA was further linearized by PmeI and transformed into *Pichia* via electroporation. The transformed cells were then selected on YPD plate with 100 μg/ml zeocin at 30° C. for two days. The picked colonies were inoculated into 5 ml YPD medium at 30° C. overnight and further amplified into 50 ml BMGY medium at 30° C. overnight. After that, the cultured medium was changed to 20 ml BMMY with 0.5% methanol to induce the target protein expression. The samples were collected at different time points for every 24 hours and at that time 0.5% methanol was added, too. The samples were then centrifuged to collect supernatants and the glucanase activities were detected using the procedure mentioned above.

To test if the TF-glucanase can be mass produced by industrial scale of fermentation, the transformed cells were inoculated into 5 ml YPD medium at 30° C. overnight. Then, the culture was amplified into 2 L YPD medium and further transferred to 19 L fermentation medium (FBSM) in a 50 L fermentor. The manipulation of *Pichia* fermentation was generally followed with the guideline from Invitrogen. During fermentation process, temperature was maintained at 30° C. and pH was fixed to 5.0 by adding ammonium hydroxide. Dissolved oxygen was maintained above 40% by air flow rate and agitation rate. After batch phase, the carbon source was added by feeding 50% glycerol. Methanol was added to induce the protein expression. The protein expression yield and glucanase activity were monitored for every 12 hours. Consequently, the glucanase activity of the V18Y/W203Y mutant was significantly higher (up to 2-fold) than that of the wild type enzyme.

Figure 8:
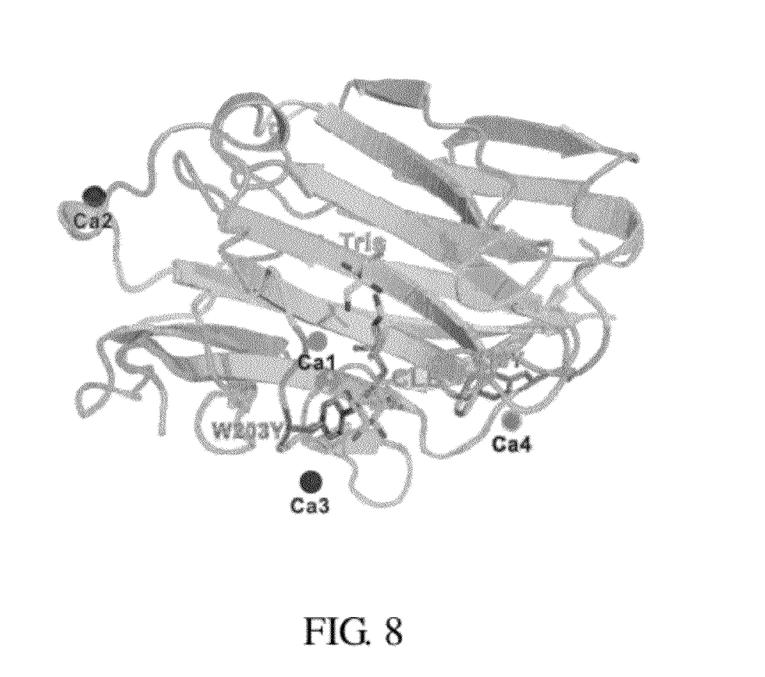
FIG. 8 shows the structure of the V18Y/W203Y mutant protein in complex with cellobiose.

To further understand how the V18Y/W203Y mutant can improve the thermostability and enzyme activity, the structure of the V18Y/W203Y mutant protein was sloved by X-ray crystallography. First, the protein crystal was obtained by using sitting drop vapor diffusion method at room temperature. The crystal was first seen from crystal screen kits and the better crystal was obtained by a condition that contained 0.1 M Tris-HCl, pH 7.5, 0.3 M Calcium acetate, and 29% PEG-SKMME. Then the crystal was soaked with mother liquor with 10 mM cellotetraose for 1 hour, and the diffraction data from the crystal were collected. After that, the crystal structure was determined by molecular replacement method using the crystallographic software of CNS program. Accordingly, the structure of the V18Y/W203Y mutant protein in complex with cellobiose (CLB) was sloved, as shown in FIG. 8.

Figure 9:
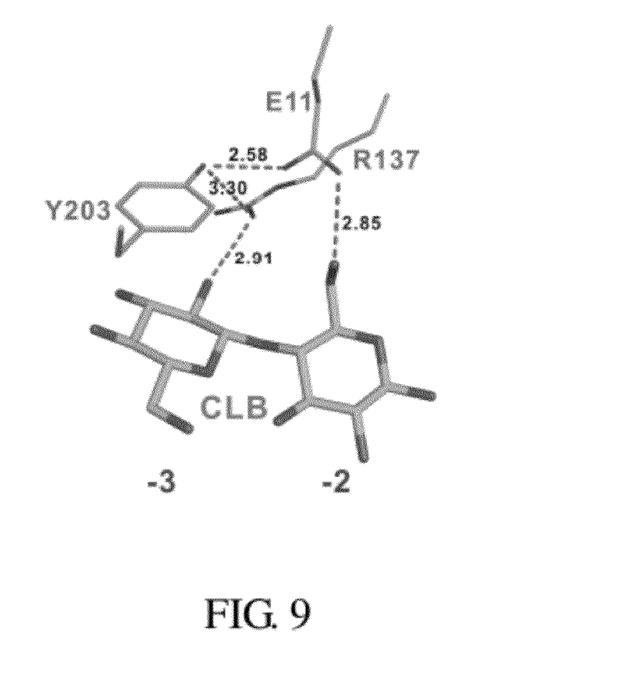
FIG. 9 shows partial structure of the V18Y/W203Y mutant protein in complex with cellobiose.

FIG. 9 shows partial structure of the V18Y/W203Y mutant protein in complex with cellobiose (CLB). As shown in the figure, there are slight conformational changes for the E11 and R137 residues. The Y203 can increase two hydrogen bonds to E11 and R137, so that these two residues might be able to keep the best position to better recognize the sugar in the −3 and −2 subsites. That might explain why W203Y mutation can increase the specific activity significantly.

Figure 10:
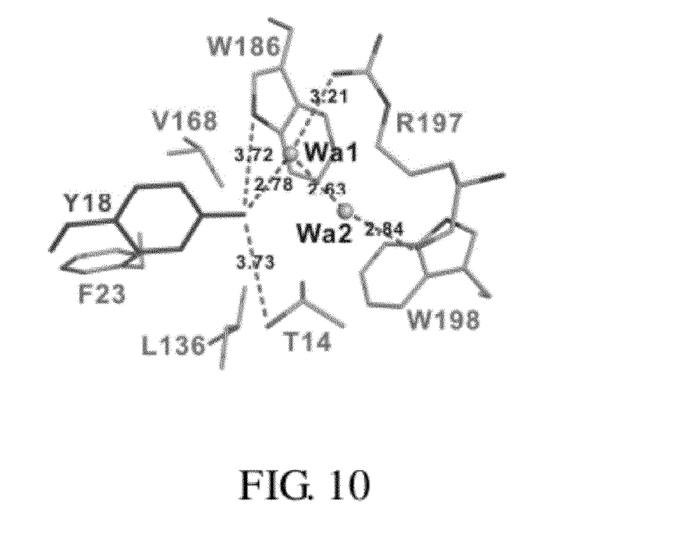
FIG. 10 shows partial structure of the V18Y/W203Y mutant protein.

FIG. 10 shows partial structure of the V18Y/W203Y mutant protein. As shown in the figure, Y18 seemed to increase the hydrophobic interactions with other residues. There were two water molecules (Wa1 and Wa2) observed in this study and did not observed in previous solved TF-glucanase structures. Y18 can also have hydrogen bonds with T14 and W186 and interact with R197 via two water molecules. That might explain why V18Y mutation can increase the thermostability of TF-glucanase.

In conclusion, the present invention designed some mutations to improve the TF-glucanase thermostability and specific activity by site-directed mutagenesis based on previous solved X-ray TF-glucanase complex structures. For the V18Y and V18Y/W203Y mutants, 2° C. increment of temperature tolerance (Tm, changed from 57 to 59° C.) was observed; that is to say, the thermostability of TF-glucanase was improved when Val18 was mutated to tyrosine. As for the W203Y and V18Y/W203Y mutants, at least 1.6-fold increase in enzyme activity compared to the wild type enzyme was observed; that is to say, the enzyme activity of TF-glucanase was improved when Trp203 was mutated to tyrosine. Except the *E. coli* expression system, the V18Y/W203Y mutant also had better glucanase activity in the industrial used yeast strain, *Pichia pastoris*, by using flask and 50 L fermentor test. Therefore, the V18Y/W203Y mutant is of much value to reduce the production costs and enhance the industrial application, especially in food industry and feed industry.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A glucanase comprising a modified amino acid sequence of SEQ ID NO: 2, wherein valine at position 18 is substituted with tyrosine and tryptophan at position 203 is substituted with tyrosine.

2. The glucanase according to claim 1 wherein a DNA encoding the amino acid sequence of SEQ ID NO: 2 is a C-terminal truncated Fsβ-glucanase DNA isolated from *Fibrobacter succinogenes*.

3. The glucanase according to claim 1 being a 1,3-1,4-β-D-glucanase.

4. The glucanase according to claim 1 having a full length amino acid sequence of SEQ ID NO: 8.

5. A glucanase comprising a modified amino acid sequence of SEQ ID NO: 2, wherein valine at position 18 is substituted with tyrosine.

6. The glucanase according to claim 5 wherein a DNA encoding the amino acid sequence of SEQ ID NO: 2 is a C-terminal truncated Fsβ-glucanase DNA isolated from *Fibrobacter succinogenes*.

7. The glucanase according to claim 5 being a 1,3-1,4-β-D-glucanase.

8. The glucanase according to claim 5 having a full length amino acid sequence of SEQ ID NO: 4.

* * * * *